(12) United States Patent
Banco et al.

(10) Patent No.: US 9,278,365 B2
(45) Date of Patent: Mar. 8, 2016

(54) VOLATILE MATERIAL DISPENSER AND METHOD OF EMITTING A VOLATILE MATERIAL

(71) Applicant: S.C. Johnson & Son, Inc., Racine, WI (US)

(72) Inventors: Michael J. Banco, Racine, WI (US); Maciej K. Tasz, Racine, WI (US); Jerome A. Matter, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 204 days.

(21) Appl. No.: 14/225,930

(22) Filed: Mar. 26, 2014

(65) Prior Publication Data

US 2015/0273500 A1    Oct. 1, 2015

(51) Int. Cl.
| | |
|---|---|
| A61L 9/12 | (2006.01) |
| B01F 3/04 | (2006.01) |
| B05B 7/24 | (2006.01) |
| A61L 9/04 | (2006.01) |
| A61L 9/05 | (2006.01) |
| A61L 9/14 | (2006.01) |
| A01M 1/20 | (2006.01) |

(Continued)

(52) U.S. Cl.
CPC ............ *B05B 7/2491* (2013.01); *A01M 1/2055* (2013.01); *A61L 9/046* (2013.01); *A61L 9/05* (2013.01); *A61L 9/12* (2013.01); *A61L 9/14* (2013.01); *B01F 3/0407* (2013.01); *B01F 3/04021* (2013.01); *A61L 2209/131* (2013.01); *A61L 2209/132* (2013.01); *A61M 11/005* (2013.01); *A61M 15/0085* (2013.01); *B05B 17/0615* (2013.01)

(58) Field of Classification Search
CPC .... B01F 3/04; B01F 3/04007; B01F 3/04021; B01F 3/0407; A61L 9/04; A61L 9/12
USPC ...................... 261/30, 72.1, 78.2, 81, 95, 101, 261/DIG. 65, DIG. 88
See application file for complete search history.

(56) References Cited

U.S. PATENT DOCUMENTS

| | | |
|---|---|---|
| 2,131,560 A | 9/1938 | Jaroll |
| 2,661,870 A | 12/1953 | Huenergardt |

(Continued)

FOREIGN PATENT DOCUMENTS

| | | |
|---|---|---|
| EP | 0836857 A1 | 4/1998 |
| EP | 1707889 | 10/2006 |

(Continued)

OTHER PUBLICATIONS

PCT/US2015/021197 International Search Report and Written Opinion dated Jun. 1, 2015.

*Primary Examiner* — Robert A Hopkins (57) ABSTRACT

A method of dispensing a fragrance having at least one aroma chemical includes the step of providing a frame adapted to be attached to a dispenser for dispensing fluids and a cartridge including a volatile material containing a fragrance comprising at least one aroma chemical, wherein the cartridge is adapted for attachment to the frame. The method of dispensing further includes the steps of nebulizing water to create nebulized water particles, directing the nebulized water particles at the cartridge, and entraining volatile material from the cartridge in at least some of the nebulized water particles upon collision with the cartridge to create volatile material-infused water particles.

20 Claims, 9 Drawing Sheets

(51) Int. Cl.
 *A61M 11/00* (2006.01)
 *A61M 15/00* (2006.01)
 *B05B 17/06* (2006.01)

(56) References Cited

U.S. PATENT DOCUMENTS

| | | | |
|---|---|---|---|
| 2,855,244 A | 10/1958 | Camp |
| 2,884,201 A | 4/1959 | Teich |
| 4,078,480 A | 3/1978 | Luck |
| 4,165,835 A | 8/1979 | Dearling |
| 4,308,241 A | 12/1981 | deVries |
| 4,732,321 A | 3/1988 | Dolan |
| 4,752,422 A | 6/1988 | Uchida et al. |
| 4,753,663 A | 6/1988 | Neefus et al. |
| 5,009,342 A | 4/1991 | Lawrence et al. |
| 5,054,477 A | 10/1991 | Terada et al. |
| 5,170,782 A | 12/1992 | Kocinski |
| 5,242,111 A | 9/1993 | Nakoneczny et al. |
| 5,501,032 A | 3/1996 | Pitman |
| 5,547,616 A | 8/1996 | Dancs et al. |
| 5,944,223 A | 8/1999 | Klima et al. |
| 5,971,210 A | 10/1999 | Brugger |
| 6,196,527 B1 | 3/2001 | Huang |
| 6,679,436 B1 | 1/2004 | Onishi et al. |
| 6,705,312 B2 | 3/2004 | Tanaka et al. |
| 6,802,460 B2 | 10/2004 | Hess |
| 6,968,124 B1 | 11/2005 | Varanasi et al. |
| 7,007,863 B2 | 3/2006 | Kotary et al. |
| 7,055,764 B1 | 6/2006 | Martinez et al. |
| 7,073,731 B2 | 7/2006 | Hess et al. |
| 7,093,775 B1 | 8/2006 | Bingham |
| 7,189,372 B2 | 3/2007 | Nohara et al. |
| 7,213,770 B2 | 5/2007 | Martens, III et al. |
| 7,281,670 B2 | 10/2007 | Lakatos et al. |
| 7,387,265 B2 | 6/2008 | Hess et al. |
| 7,451,895 B2 | 11/2008 | Newton |
| 7,597,309 B1 | 10/2009 | Stucki |
| 7,677,536 B2 | 3/2010 | Wang et al. |
| 7,758,026 B2 | 7/2010 | Kulcke et al. |
| 7,819,336 B2 | 10/2010 | Newman |
| 7,832,655 B2 | 11/2010 | Tollens et al. |
| 7,887,759 B2 | 2/2011 | Triplett |
| 7,913,933 B2 | 3/2011 | Van Roemburg |
| 7,942,644 B2 | 5/2011 | Young et al. |
| 7,963,460 B2 | 6/2011 | Jorgensen |
| 8,136,700 B2 | 3/2012 | LaFlamme et al. |
| 8,156,933 B2 | 4/2012 | Raghurprasad |
| 8,196,903 B2 | 6/2012 | Jorgensen |
| 8,430,337 B2 | 4/2013 | Pearce, III et al. |
| 8,474,659 B2 | 7/2013 | Dennis |
| 2002/0004033 A1 | 1/2002 | Sorgenfrey |
| 2002/0020761 A1 | 2/2002 | Jordan |
| 2002/0148911 A1 | 10/2002 | Beck et al. |
| 2005/0025738 A1 | 2/2005 | Hall |
| 2008/0223953 A1 | 9/2008 | Tomono et al. |
| 2008/0251599 A1 | 10/2008 | Ward et al. |
| 2011/0156288 A1 | 6/2011 | Ahn |
| 2011/0215008 A1 | 9/2011 | Carroll |
| 2011/0232321 A1 | 9/2011 | Bortoletto et al. |
| 2011/0290241 A1 | 12/2011 | Maeda et al. |
| 2011/0309157 A1 | 12/2011 | Yang et al. |
| 2012/0018529 A1 | 1/2012 | Gammon et al. |
| 2012/0159806 A1 | 6/2012 | Dana |
| 2012/0241987 A1 | 9/2012 | Lee |
| 2013/0037020 A1 | 2/2013 | Tanaka et al. |
| 2013/0079732 A1 | 3/2013 | Burt et al. |
| 2013/0079733 A1 | 3/2013 | Burt et al. |
| 2013/0106004 A1 | 5/2013 | Stumphauzer |
| 2013/0334336 A1 | 12/2013 | Haran et al. |
| 2014/0041524 A1 | 2/2014 | Talbot et al. |

FOREIGN PATENT DOCUMENTS

| | | | |
|---|---|---|---|
| JP | 03247344 A | * | 11/1991 |
| KR | 20020037017 | | 5/2002 |
| WO | WO 2012066068 | | 5/2012 |
| WO | WO 2013070441 | | 5/2013 |

* cited by examiner

|  | |
|---|---|
| Aroma chemicals in this range will be biased to delivery via pathway #1: direct evaporation to the air | Aroma chemicals in this range will be biased to delivery to the air by any pathway of "least resistance", and may show high delivery rates |
| Aroma chemicals in this range will be biased to delivery to the air by any pathway of "least resistance", but may show low delivery rates | Aroma chemicals in this range will be biased to delivery via pathway #3: infusion to water followed by nebulization to air |

Volatility: High / Low
Water Solubility: Low / High

| Lavender & Peach Blossom | | | Vanilla | | |
|---|---|---|---|---|---|
| Sample 1 | Sample 2 | Sample 3 | Sample 1 | Sample 2 | Sample 3 |
| 10 mg/hr | 14 mg/hr | 22 mg/hr | 10 mg/hr | 11 mg/hr | 20 mg/hr |

| Nectar Blossoms | | | Attraction | | |
|---|---|---|---|---|---|
| Sample 1 | Sample 2 | Sample 3 | Sample 1 | Sample 2 | Sample 3 |
| 9 mg/hr | 18 mg/hr | 32 mg/hr | 12 mg/hr | 8 mg/hr | 15 mg/hr |

FIG. 9

VOLATILE MATERIAL DISPENSER AND METHOD OF EMITTING A VOLATILE MATERIAL

BACKGROUND

1. Field of the Disclosure

The present invention relates generally to volatile material dispensers and, more particularly, to volatile material dispensers that mix water and volatile materials.

2. Description of the Background

Various volatile material dispensers are known in the prior art, most of which deliver fragrance to the air by a number of different mechanisms, including, for example: (1) the fragrance is sprayed into the air or (2) the fragrance is evaporated into the air. Such volatile material dispensers generally include a housing with a refill inserted therein. The refill generally includes a container for holding a volatile material, wherein the volatile material may include various components including aroma chemicals, water, solvents, surfactants, alcohols, and other components. Some refills include a wick in contact with the volatile material and extending out of the refill to carry the volatile material out of the refill. Other refills include a gel-like substance that is emitted through a semi-permeable membrane. Regardless of the type of refill, a refill may be inserted into a volatile material dispenser having a heater, a piezoelectric element, an aerosol actuator, or any other diffusion element that may assist in delivering the volatile material.

For volatile material dispensers that are evaporation-based, a perfumer or developer of fragranced volatile materials for the dispensers must select aroma chemicals (forming the fragrance) that are sufficiently volatile for the particular delivery system (i.e., heater-based, passive, fan-based, etc.). Similarly, if the volatile material dispenser is spray-based, the perfumer must choose aroma chemicals (forming the fragrance) that work with the bulk liquid of the spray (e.g., solubility parameters are important). The constraints in such dispensers limit the types of aroma chemicals that may be used in such dispensers.

SUMMARY

In illustrative embodiments, a method of dispensing a fragrance having at least one aroma chemical may include the step of providing a frame adapted to be attached to a dispenser for dispensing fluids and a cartridge including a volatile material containing a fragrance comprising at least one aroma chemical, wherein the cartridge is adapted for attachment to the frame. The method of dispensing may further include the steps of nebulizing water to create nebulized water particles, directing the nebulized water particles at the cartridge, and entraining volatile material from the cartridge in at least some of the nebulized water particles upon collision with the cartridge to create volatile material-infused water particles.

In other illustrative embodiments, a volatile material dispenser may include a frame adapted to be attached to a dispenser having an ultrasonic nebulizer for dispensing fluids. The dispenser may further include a cartridge containing a volatile material and adapted to be attached to the frame, wherein the frame is adapted to position the cartridge within the dispenser such that the cartridge is in a path of the nebulized water particles, whereby the cartridge acts a baffle that filters out larger nebulized fluid particles emitted by the ultrasonic nebulizer.

In further illustrative embodiments, a volatile material dispenser may include a housing having a reservoir adapted to hold water and an ultrasonic nebulizer in communication with the reservoir and the water within the reservoir, wherein the ultrasonic nebulizer is adapted to volatilize and emit the water as nebulized water particles. The dispenser may further include a cartridge containing a volatile material and positioned such that nebulized water particles from the ultrasonic nebulizer impinge upon the cartridge and entrain volatile material within the nebulized water particles, wherein the volatile material comprises a fragrance with at least one aroma chemical and the volatile material is free of solvents and surfactants.

BRIEF DESCRIPTION OF THE DRAWINGS

Other aspects and advantages of the present invention will become apparent upon consideration of the following detailed description, wherein similar structures have like or similar reference numerals.

DETAILED DESCRIPTION

The present disclosure is directed to volatile material dispensers that are capable of mixing water and volatile materials. While the present application may be embodied in many different forms, several specific embodiments are discussed herein with the understanding that the present application is to be considered only as an exemplification of the principles of the application, and it is not intended to limit the application to the embodiments illustrated.

Figure 1:
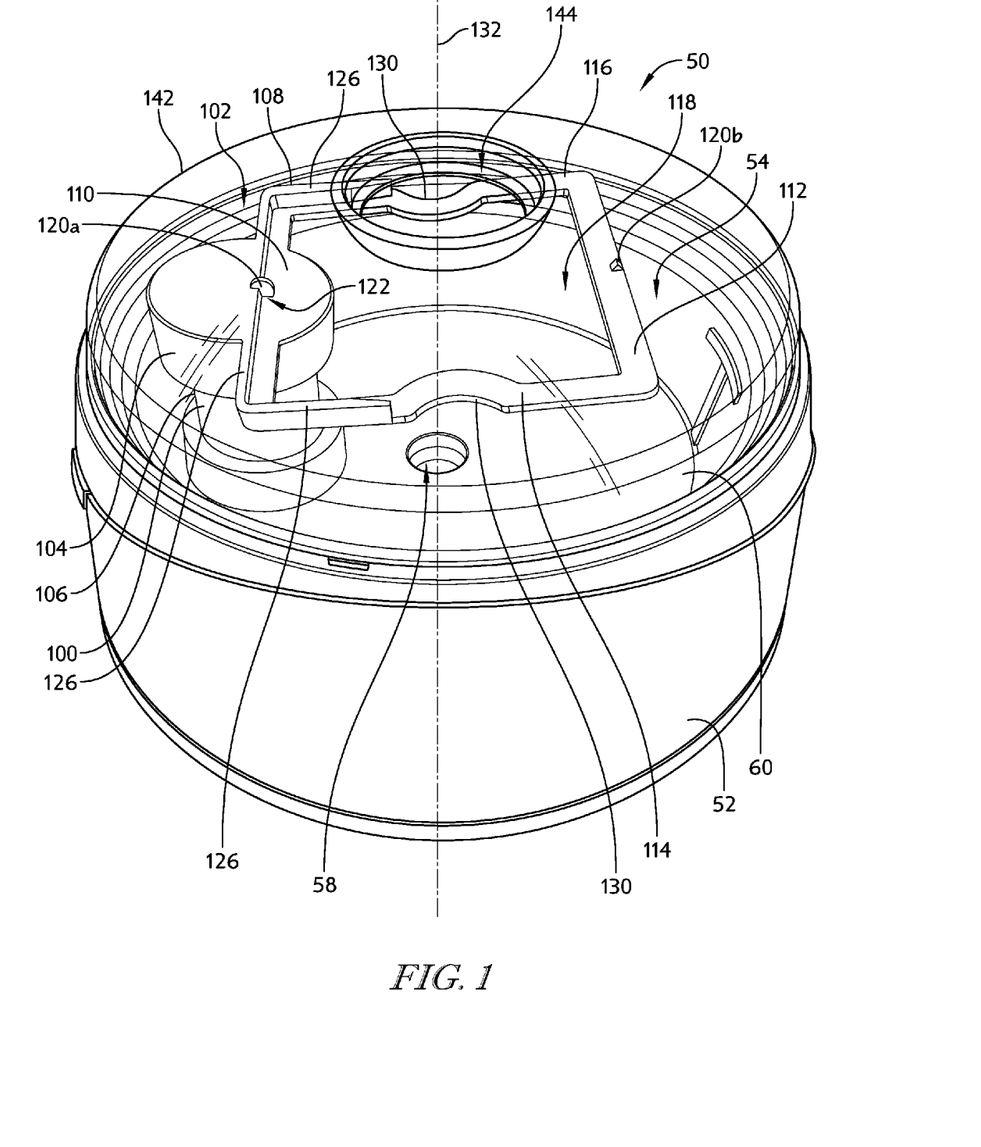
FIG. 1 is top perspective view of an exemplary dispenser embodying the principles of the present application.
Figure 2:
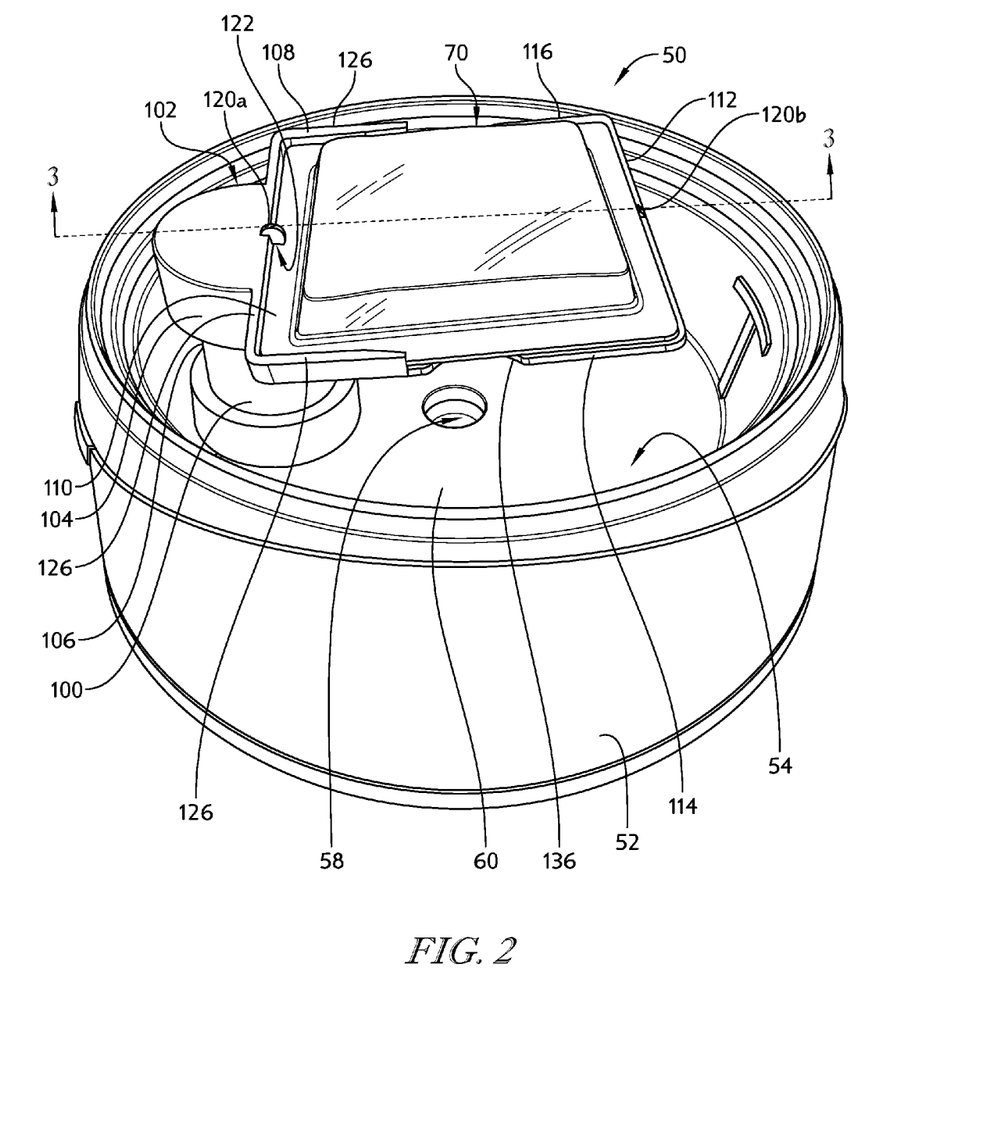
FIG. 2 is a top perspective view of the dispenser of FIG. 1 with a cover removed therefrom and a cartridge attached to a cartridge holder within the dispenser.
Figure 3:
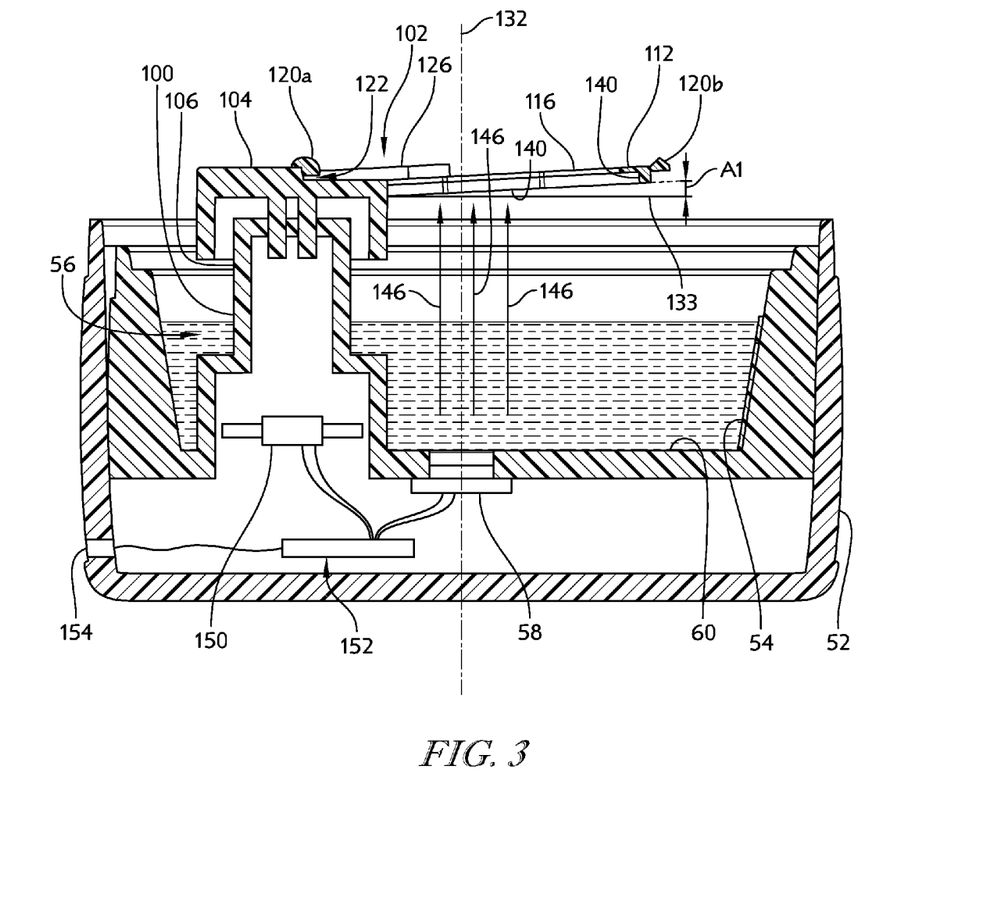
FIG. 3 is a cross-sectional view taken generally along the lines 3-3 of FIG. 2 and depicting various internal components of the dispenser.

Referring to the drawings, FIGS. 1-3 depict a volatile material dispenser 50 for combining water and volatile materials for dispensing. The volatile material dispenser 50 generally includes a housing 52 having a reservoir 54 for holding water 56. An ultrasonic nebulizer 58, or any other suitable device for emitting one or more materials as a mist, is disposed within or adjacent the reservoir 54 so as to be submerged in the water 56 within the reservoir 54. In an illustrative embodiment, the ultrasonic nebulizer 58 may be disposed within a bottom wall 60 of the reservoir 54 with a top surface of the ultrasonic nebulizer 58 in contact with the water 56. In other illustrative embodiments, the ultrasonic nebulizer 58 may be positioned in any suitable location within the ultrasonic nebulizer 58 for aerosolizing the water 56.

Figure 4:
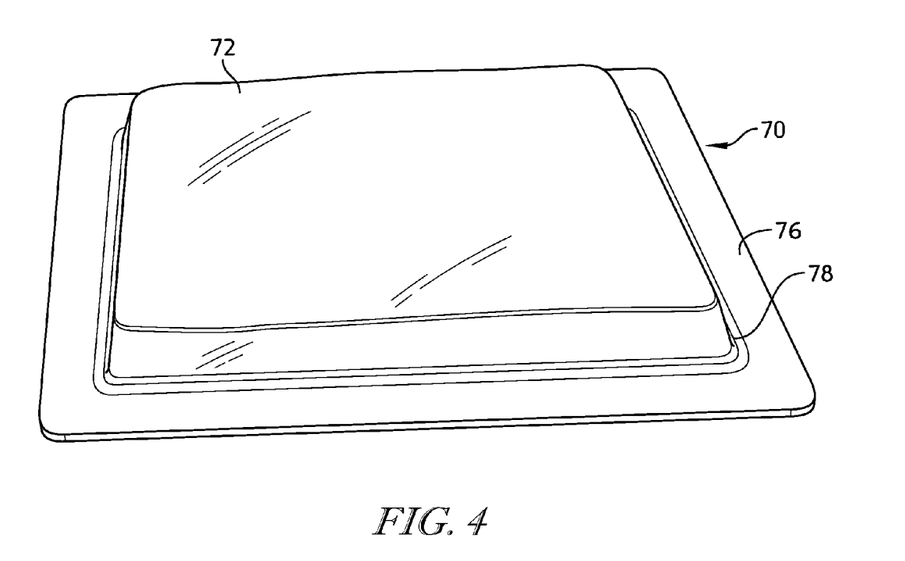
FIG. 4 is a top perspective view of the cartridge of FIG. 2.
Figure 5:
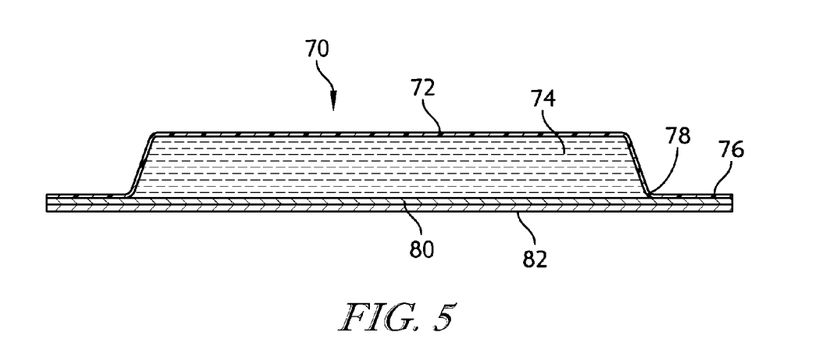
FIG. 5 is a cross-sectional view taken generally along the lines 5-5 of FIG. 4 and depicting components of the cartridge.

As best seen in FIGS. 2-5, a volatile material cartridge 70 is disposed within the housing 52, for example, above the reservoir 54 or within the reservoir 54. In an illustrative embodiment, the cartridge 70 is spaced from the water 56 within the reservoir 54. Similarly, the cartridge 70 is spaced from the bottom wall 60 of the reservoir 54. In illustrative embodiments, as best seen in FIGS. 4 and 5, the cartridge 70 includes a plastic tray 72 for holding a liquid or gel volatile material 74 (FIG. 5) and having a peripheral flange 76 extending outwardly from an upper edge 78 of the plastic tray 72. The plastic tray 72 and the peripheral flange 76 may be formed of a recycled polyethylene terephthalate (RPET) layer adhesively bonded to a nylon laminate, wherein the nylon laminate may include a layer of ethylene vinyl acetate (EVA) coextruded to each side of a middle nylon layer. Optionally, the plastic tray 72 and the peripheral flange 76 may be made from any other suitable non-porous, non-permeable material.

Still referring to FIGS. 4 and 5, a non-porous permeable membrane 80 may be attached to the peripheral flange 76 to cover the plastic tray 72. In illustrative embodiments, the permeable membrane 80 may be comprised of a low density polyethylene (LDPE) or any other suitable material. An impermeable membrane 82 may be releasably adhered to the peripheral flange 76 over the non-porous permeable membrane 80. In illustrative embodiments, the impermeable membrane 82 is formed of foil or any other suitable material. During use, the impermeable membrane 82 may be removed to allow the volatile material 74 to escape through the non-porous permeable membrane 80. In illustrative embodiments, a cartridge sold by S. C. Johnson & Son, Inc. under the trademark Glade Sensations® may be used or a cartridge as disclosed in Martens, I I I et al. U.S. Pat. No. 7,213,770, issued on May 8, 2007, and entitled "Volatile Material Dispensing System" may be used. While a particular cartridge 70 is disclosed and depicted herein, any other suitable cartridge or refill may be utilized without departing from the scope of the present application.

The volatile material 74 within the cartridge 70 may include one or more active ingredients. Exemplary active ingredients include, but are not limited to, one or more of a cleaner, an insecticide, an insect repellant, an insect attractant, a disinfectant, a mold or mildew inhibitor, an antimicrobial, a fragrance comprised of one or more aroma chemicals, a disinfectant, an air purifier, an aromatherapy scent, an antiseptic, an odor eliminator, a positive fragrancing active material, an air-freshener, a deodorizer, a medicinal component, an inhalant (e.g., for relieving a cough or congestion), or the like, and combinations thereof.

The volatile material 74 may be in any form that, in combination with the structure of the cartridge 70, prevents leaking, dripping, or flowing of the volatile material 74 from the cartridge 70 and may provide a slow, passive diffusion into the surrounding atmosphere. In illustrative embodiments, the volatile material 74 is in the form of a gel including a fragrance and/or insecticide, and further comprising at least one dye and a thickening agent that color and thicken the volatile material 74, respectively. In illustrative embodiments, the volatile material is free of solvents and surfactants.

As best seen in FIGS. 1 and 3, a hollow post 100 may extend upwardly from the bottom wall 60 of the reservoir 54. A cartridge holder 102 includes a cap 104 that is detachably attached to a top end 106 of the post 100 in any suitable manner and a frame 108 for attachment of the cartridge 70. In illustrative embodiments, the frame 108 may include first and second opposing side edges 110, 112 and third and fourth opposing side edges 114, 116 extending between the first and second opposing side edges 110, 112. An opening 118 may be formed in a central portion of the frame 108 between the side edges 110, 112, 114, 116.

As seen in FIG. 1, one or more projections 120a, 120b may extend from any number of the side edges 110, 112, 114, 116 to aid in retaining and orienting the cartridge 70 on the frame 108. More specifically, when a user desires to emit volatile material 74 from the dispenser 50, the user may insert the cartridge 70 by removing the cartridge holder 102 from the post 100 and attaching the cartridge 70 to the frame 108 or attaching the cartridge 70 to the frame 108 while the cartridge holder 102 is attached to the post 100. Regardless of the manner in which the cartridge 70 is attached, the projections 120a, 120b force a user to insert the cartridge 70 with the non-porous permeable membrane 80 facing the bottom wall 60 of the reservoir 54. In particular, the projection 120a creates a small gap 122 between the projection 120a and the first side edge 110 that may accommodate the peripheral flange 76 of the cartridge 70. Upon insertion of the cartridge 70 with the plastic tray 72 facing downwardly, the cap 104 of the cartridge holder 102 interferes with the downwardly extending plastic tray 72 to prevent insertion with the plastic tray 72 facing downwardly. In contrast, when the peripheral flange 76 is inserted into the gap 122 with the non-porous permeable membrane 80 facing toward the bottom wall 60 of the reservoir 54, the peripheral flange 76 of the cartridge 70 creates a planar surface that fits against the side edges 110, 112, 114, 116 for proper insertion of the cartridge 70 into the frame 108. In illustrative embodiments, one or more of the sides edges 110, 112, 114, 116 may include full or partial upwardly extending walls 126 that additionally assist in positioning the cartridge 70 on the frame 108. While particular positioning features are disclosed, other suitable positioning features may additionally or alternatively be utilized to position the cartridge 70 on the frame 108.

In illustrative embodiments, the cartridge 70 is positioned with the cartridge 70 disposed above the ultrasonic nebulizer 58 and the ultrasonic nebulizer 58 horizontally centered with respect to the cartridge 70. In further illustrative embodiments, the ultrasonic nebulizer 58 may not be centered with respect to the cartridge 70. The cartridge 70 may be placed above the ultrasonic nebulizer 58 and/or above the water 56 to allow nebulized water to be projected upwardly at the cartridge 70, as will be discussed in greater detail hereinafter.

When the volatile material 74 within the cartridge 70 is gone or the user no longer desires volatile material 74, the cartridge 70 may be removed in a manner similar to the manner the cartridge 70 was inserted into the frame 108. As best seen in FIG. 1, notches 130 are formed in the third and fourth side edges 114, 116 of the frame 108 to assist a user in grasping the peripheral flange 76 of the cartridge 70.

As further seen in FIG. 3, the bottom wall 60 of the reservoir is generally orthogonal to a longitudinal axis of the dispenser 50. The frame 108 is spaced from the bottom wall 60 and may be disposed at an angle A1 with respect to a horizontal plane 133 that is generally orthogonal to a longitudinal axis 132 of the dispenser 50 and parallel to the bottom wall 60 of the reservoir 54. While A1 is shown such that a free end of the frame 108 tilts upwardly (positive angle A1), the free end of the frame 108 may alternatively tilt downwardly (negative angle A1). In illustrative embodiments, the angle A1 may be between about −15 degrees and about 15 degrees. In other illustrative embodiments, the angle A1 may be between about −10 degrees and about 10 degrees. In still other illustrative embodiments, the angle A1 may be between about −5 degrees and about 5 degrees. In other illustrative embodiments, the frame 108 may be tilted to one side or the other at angles similar to the angles described above with respect to the angle A1. In further illustrative embodiments, the frame 108 may be tiled to one side and may further be tilted upwardly or downwardly. As will be discussed in more detail below during a discussion of the operation of the dispenser 50, the angle A1 (and/or tilting to either side) is designed to allow water condensing on a bottom of the cartridge 70 to runoff and drip back into the reservoir 54 in a uniform and consistent manner.

Still referring to FIG. 3, one or more partial or continuous stiffening ribs 140 may be disposed on bottom surfaces of one or more of the first, second, third, and fourth side edges 110, 112, 114, 116. The stiffening ribs 140 provide rigidity to the frame 108 and aid in retaining the frame 108 at the angle A1. In illustrative embodiments, the ribs 140 extend downwardly from each of the first, second, third, and fourth side edges 110, 112, 114, 116 and are connected to one another such that the ribs 140 extend around the entire frame 108.

As seen in FIG. 1, the dispenser 50 may include a cover 142 that is removably attached to the housing 52. If a cover 142 is utilized, an aperture 144 may be disposed through at least a portion of the cover 142 for emission of water and volatile material therethrough. If used, the cover 142 may be removed to refill the water 76 in the reservoir 54 and/or to replace the cartridge 70. In illustrative embodiments, a retention feature (not shown) may be utilized to prevent inadvertent removal of the cover 142 from the housing 52, but allow removal of the cover 142 when desired. Such retention feature may include one or more of detents, latches, clips, and/or any other suitable retention feature(s).

The dispenser 50 may include any suitable circuitry 152 that controls the operation of the ultrasonic nebulizer 58. In illustrative embodiments, the circuitry 152 operates the ultrasonic nebulizer 58 in a constant manner. In other illustrative embodiments, the circuitry 152 may control the ultrasonic nebulizer 58 to run intermittently, at increasing or decreasing intervals, or in any other constant or varied manner. The dispenser 50 may include a number of batteries (not shown) for powering the components of the dispenser 50 and/or may include any suitable plug 154 for connection of a power cord (not shown).

In illustrative embodiments, the dispenser 50 may further include a blower 150 that may be any suitable device that moves air. In illustrative embodiments, the blower 150 is operatively connected to the circuitry 152, which is programmed to run the blower 150 at different speeds. In illustrative embodiments, such different speeds may include a steadily increasing speed, a pulsed speed, alternating speeds (e.g., on and off or slow and fast), or any other varied or constant speed(s). Increasing fan speeds may be used to steadily increase fragrance delivery over time and alternating speeds may provide bursts of fragrance over time, both of which promote long-lasting noticeability.

The dispenser 50 may further include a sensor (not shown) that detects a low or empty level (of water) within the reservoir 54. The sensor may be located in any suitable location within or adjacent the reservoir 54. When a low or empty level (of water) in the reservoir 54 is detected, the circuitry 152 may be programmed to turn off one or more of the ultrasonic nebulizer 58, the blower 150, and/or any other components of the dispenser 50. After the ultrasonic nebulizer 58 and/or blower 150 are turned off, the fragrance (and its aroma chemical components) in the cartridge 70 continues to passively evaporate into the dispenser 50. When the dispenser 50 is again turned on, the fragrance collected in the dispenser 50 will be evacuated, giving the user an initial burst of fragrance that signals the dispenser 50 is functioning.

In use, water 56 is placed within the reservoir 54 to be nebulized by the ultrasonic nebulizer 58. The dispenser 50 may be actuated before or after insertion of the cartridge 70. As noted above, the cartridge 70 may be placed above the ultrasonic nebulizer 58 to allow nebulized water to be projected upwardly at the cartridge 70, as seen by the arrows 146 in FIG. 3. In this manner, the cartridge 70 acts as a baffle. More particularly, during operation of the dispenser 50, the ultrasonic nebulizer 58 may be periodically or continuously energized to nebulize and spray the water 56 within the reservoir 54. The nebulized water is sprayed directly at the cartridge 70. In illustrative embodiments, an optional blower 150 may be disposed within the reservoir 54 or adjacent the reservoir to assist in moving the nebulized water toward the cartridge 70 and/or out of the dispenser 50.

Figure 6A:
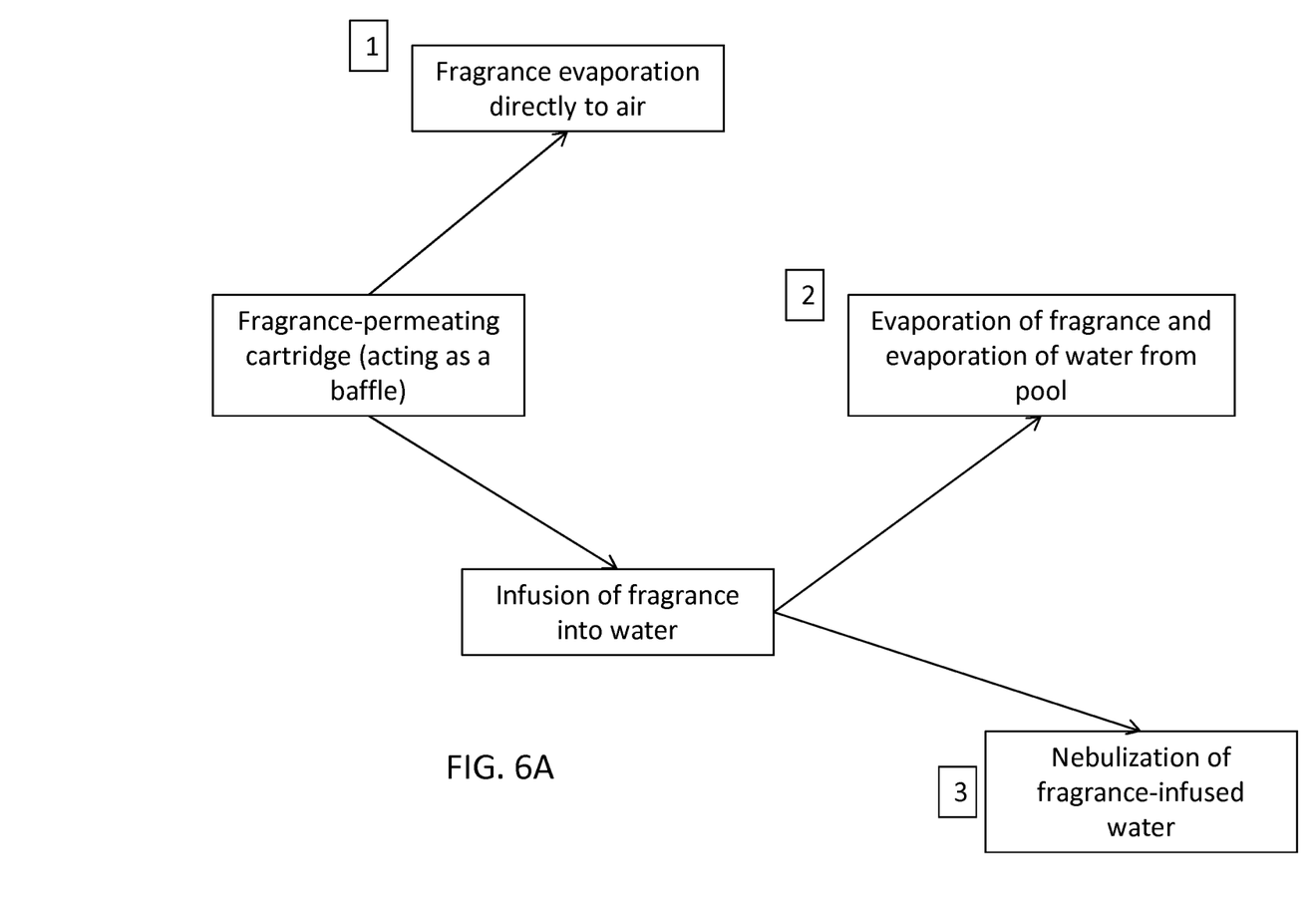
FIG. 6A is a diagram of exemplary pathways in which aroma chemicals may be emitted into the air by any of the dispensers of the present application.
Figure 6B:
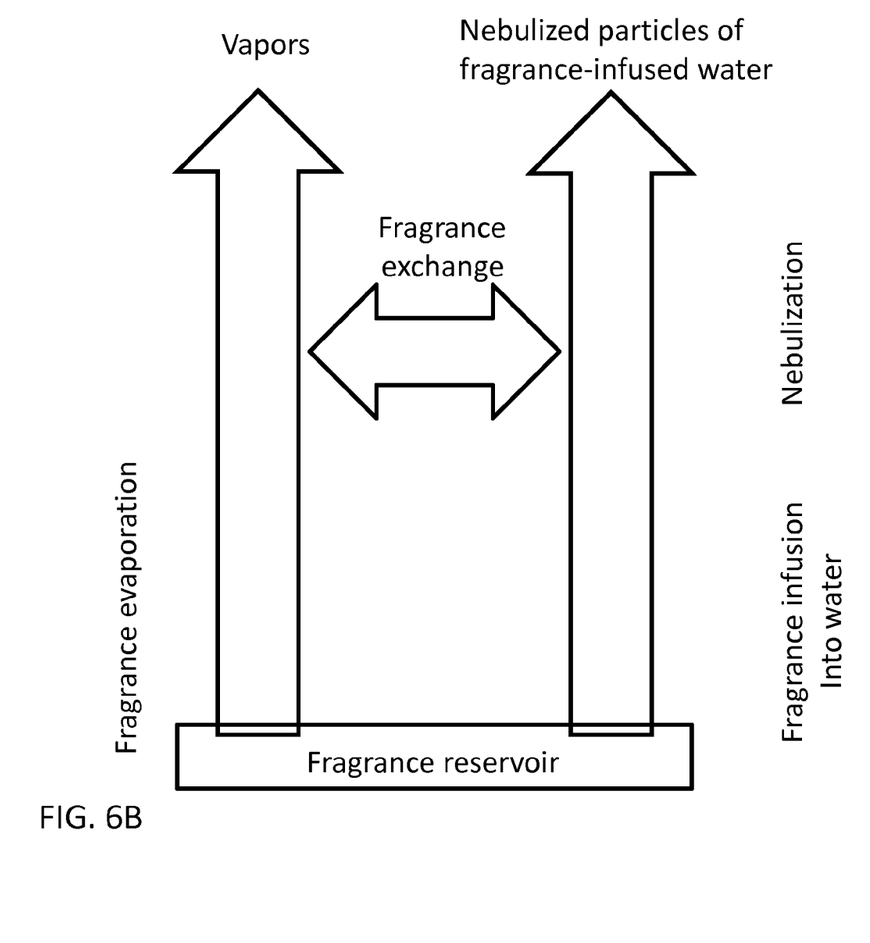
FIG. 6B is diagram illustrating an alternative manner in which to depict the exemplary pathways in which aroma chemicals may be emitted into the air of FIG. 6A.

In an example in which the volatile material includes a fragrance having one or more aroma chemicals, the cartridge 70 provides fragrance in multiple ways, as seen in FIGS. 6A and 6B. First, the aroma chemical(s) within the cartridge 70 are passively emitted through the non-porous permeable membrane 80 of the cartridge 70 (see (1) in FIG. 6A). In addition, nebulized water particles forcibly hit the cartridge 70, which acts as a baffle. Some of the nebulized water particles pick up the aroma chemical(s) 74 through an infusion-extraction process that occurs upon hitting the non-porous permeable membrane 80 and the fragrance-infused particles are emitted from the dispenser 50 (see also (1) in FIG. 6A). Other of the nebulized water particles forcibly hit the cartridge 70 acting as a baffle, condense on the non-porous permeable membrane 80 and/or other portions of the cartridge 80, and drip back into the water 56, thereby creating a fragranced water. Second, the fragranced water is later emitted passively from the reservoir 54 by evaporation of the aroma chemical(s) and water from the reservoir 54 (see (2) in FIG. 6A). Third, the fragranced water in the reservoir 54 is nebulized and emitted by the ultrasonic nebulizer 58 (see (3) in FIG. 6A).

Figure 7:
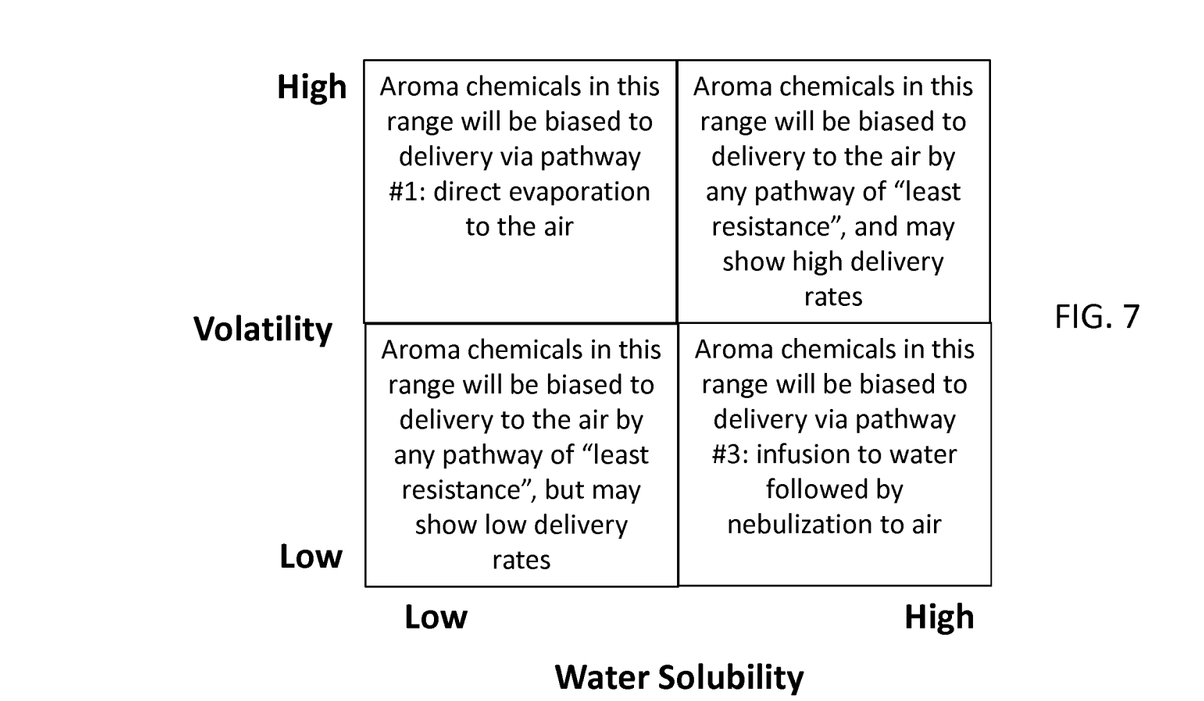
FIG. 7 is a diagram depicting the exemplary pathways taken by aroma chemicals having different volatilities and water solubilities.

The cartridge 70 adds fragrance including one or more aroma chemicals to the nebulized water and also acts to filter out larger nebulized water particles (allowing the smaller particles to stay within the airstream and be dispensed from the device). The larger water particles collide with the cartridge 70, agglomerate into even larger particles, return to the reservoir 54 (with volatile material entrained therein), and are eventually recirculated through nebulization. The smaller particles remain airborne and minimize fall-out or dropping of particles onto surfaces surrounding the dispenser 50.

The volatile material compositions 74 of the present application may include any volatile material composition, regardless of the volatility or the solubility of the composition. In illustrative embodiments utilizing fragrances with one or more aroma chemicals, any aroma chemical or combination of aroma chemicals may be utilized regardless of their volatility or solubility. Providing different methods or pathways for volatilization, as described above, allows the aroma chemicals in the volatile material compositions 74 to be emitted regardless of their volatility and/or solubility. As seen in FIG. 7, each of the aroma chemicals will make its way into the air via the manner most suitable for that aroma chemical. More specifically, the aroma chemicals with a high volatility and low water solubility will be biased to delivery via direct evaporation (either passively or through nebulized water particles hitting the cartridge 70). Aroma chemicals with a high water solubility and a low volatility will be biased toward delivery via nebulization of water from the reservoir 54 that has been infused with fragrance. Aroma chemicals with a low water solubility and low volatility will be biased toward delivery by any pathway of "least resistance", but may show low delivery rates. Lastly, aroma chemicals with a high water solubility and low volatility will be biased toward delivery by any pathway of "least resistance", but may show high delivery rates.

In determining low/high volatility chemicals and low/high water solubility chemicals, a database of 171 aroma chemicals most commonly used in home fragrancing was analyzed. High volatility aroma chemicals were defined as those aroma chemicals having a vapor pressure greater than or equal to the seventieth (70) percentile for the data set (or a vapor pressure of greater than or equal to about 1.0E-01 hectopascal (hPa)) and low volatility aroma chemicals were defined as those aroma chemicals having a vapor pressure less than or equal to the thirtieth (30) percentile for the data set (or a vapor pressure of less than or equal to about 7.5E-03 hPa). Low solubility aroma chemicals were defined as those aroma chemicals having a solubility greater than or equal to the seventieth (70) percentile for the data set (or a solubility of greater than or equal to about 3.97 Log P) and high solubility aroma chemicals were defined as those aroma chemicals having a solubility less than or equal to the thirtieth (30) percentile for the data set (or a solubility of less than or equal to about 2.6 Log P).

Examples of high volatility and low water solubility chemicals are iso-bornyl acetate (with a molecular weight of 196, a solubility of 4.3 Log P, and a volatility or vapor pressure of 1.00E-01 hPa) and limonene (with a molecular weight of 136, a solubility of 4.38 Log P, and a volatility or vapor pressure of 1.93E+00 hPa). An example of a low volatility and low water solubility chemical is lilial (with a molecular weight of 204, a solubility of 4.4 Log P, and a volatility or vapor pressure of 5.00E-03 hPa). An example of a high volatility and high water solubility chemical is methyl benzoate (with a molecular weight of 136, a solubility of 2.1 Log P, and a volatility or vapor pressure of 5.00E-01 hPa). Examples of low volatility and high water solubility chemicals are cinnamic alcohol (with a molecular weight of 134, a solubility of 2 Log P, and a volatility or vapor pressure of 4.00E-03 hPa), methy cyclopetenone (with a molecular weight of 112, a solubility of 1.29 Log P, and a volatility or vapor pressure of 1.14E-03 hPa), and sulfurol (with a molecular weight of 143, a solubility of 1.11 Log P, and a volatility or vapor pressure of 2.28E-03 hPa).

The multiple pathways for volatilization described above and shown in FIG. 6 create unique, consumer-preferred fragrance experiences and eliminate issues associated with creating fragrances for a delivery system that can only tolerate water-soluble aroma chemicals or only tolerate highly volatile aroma chemicals.

In an illustrative study, test chambers were used that were made of steel and 200 cubic feet in size with no air circulation. Each sample, as will be detailed below, was placed in its respective chamber two hours before panelists in the study began their evaluations. The samples remained in the chambers throughout the test period (blinded from the panelists). The panelists assessed smell in the chambers by opening a small door into the chamber and placing their noses inside to sniff. The panelists did not enter the chambers. After smelling a particular chamber, the panelist was asked, "How strong is the fragrance?" and were asked to rate the perceived fragrance intensity within the chamber on a scale of 1 to 7 (with 1 being weak and 7 being strong).

The order of presentation of the samples to the panelists was randomized. The study consisted of three samples: (1) a fragrance infused water (about 99.9% water and balance of fragrance oil) delivered by a piezoelectric-mesh nebulizer sold by Homedics under the item model number HUM-CM10 (the fragrance-infused water was created by submerging the cartridge 70 in water for a week before the study and then the resulting fragrance-infused water was nebulized into the air); (2) fragrance emanating from the cartridge 70 at room temperature; and (3) fragrance emanating from the cartridge 70 heated by a dispenser having a heater. Each of the chambers was kept at 68 degrees Fahrenheit (20 degrees Celsius). Various scents were also utilized for each sample including, Lavender & Peach Blossoms, Attraction, Vanilla, and Nectar Blossoms, all of which have been or are currently sold under the Glade® trademark by S. C. Johnson & Son, Inc.

Figure 8:
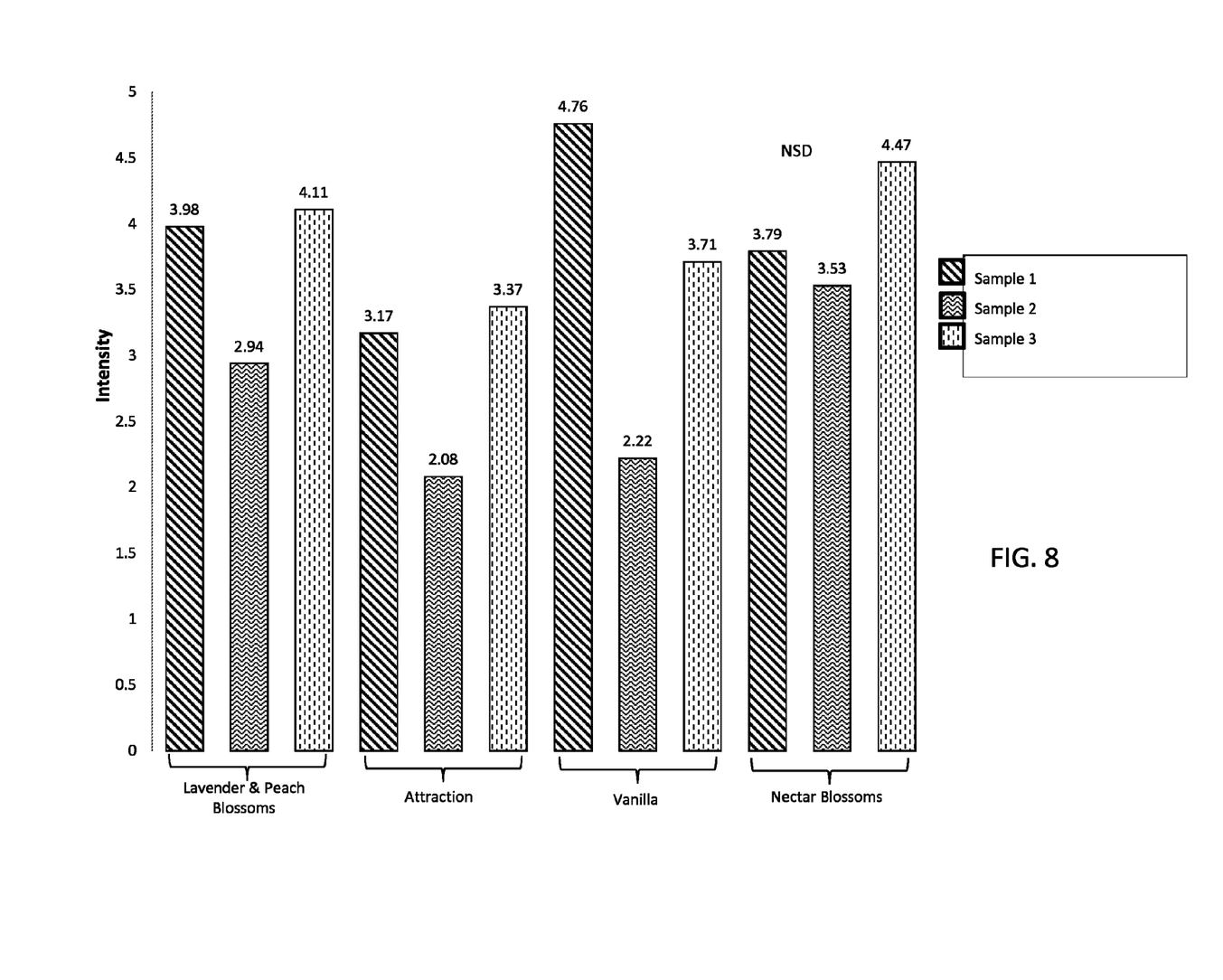
FIG. 8 is a graph depicting perceived intensity by way of a fragrance-infused water, a passively evaporated fragrance cartridge, and an actively evaporated fragrance cartridge for different fragrances.
Figure 9:
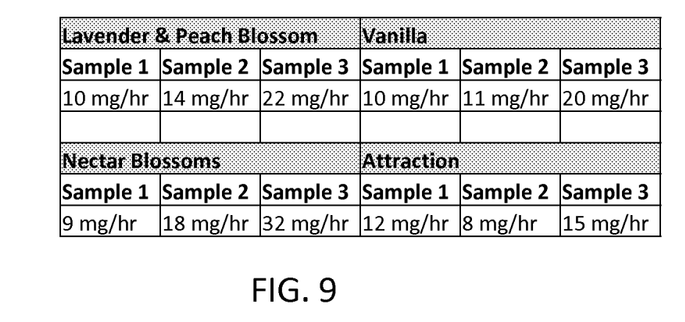
FIG. 9 is a chart detailing the fragrance delivery rates for the samples of FIG. 8 for four different fragrances.

The study was designed so that the mass fragrance delivery rate of each fragrance composition was about the same for Samples 1 and 2. As shown in the graph of FIG. 8, which depicts average fragrance intensity ratings for each of Samples 1-3 for each of the four evaluated fragrances, the fragranced-infused water (Sample 1) was perceived as significantly more intense than the passively emitted cartridge 70 (Sample 2) for three of the four evaluated fragrances (Lavender & Peach Blossoms, Attraction, and Vanilla), even though the delivery rate for Samples 1 and 2 was about the same (see FIG. 9). While the average fragrance intensity for the fragrance Nectar Blossoms for Sample 1 was not perceived as being significantly more intense than for Sample 2, the average intensity rating for Sample 1 was nominally higher than the average intensity rating for Sample 2. The fragrance delivery rates for each of Samples 1-3 for each of the fragrances is shown in FIG. 9.

Still referring to FIG. 8, the average intensity rating for Sample 1 was significantly higher than the average intensity rating for Sample 3 for the Vanilla fragrance. This is notable, as the mass fragrance delivery rate for Sample 3 (which was 20 milligrams per hour for the Vanilla fragrance) was significantly higher than the mass fragrance delivery rate for Sample 1 (which was 10 milligrams per hour for the Vanilla fragrance).

The dispensers described herein are more dynamic that typical fragrance dispensers. First, as described above, multiple pathways for emission of fragrance from the dispenser 50 are provided. Additionally, other system dynamics provide for a dynamic dispenser. In illustrative embodiments, some of the dynamic components of the dispenser 50 include, but are not limited to, the water 56 in the reservoir 54 depleting during usage, the delivery rate changing as a water level in the reservoir 54 changes, and a temperature of the water 56 in the reservoir 54 increasing over time. All of these changes vary the overall fragrance delivery rate of the dispenser 50 over time. The net result is a dynamic fragrancing dispenser, wherein the dynamics may be leveraged to create unique and differentiated fragrance experiences, which may promote long-lasting noticeability.

One of the advantages of the dispensers as disclosed herein, which include fragrance-infused water, is that the fragrance delivery to the water 56 within the reservoir 54 is dictated by the solubility dynamics of the dispenser 50. The inherent physics of, for example, the dispenser 50, significantly minimize (or possibly prevent) the accumulation of an oil slick on top of the water 56, which occurs in dispensers in which a fragranced oil is delivered directly to the water. An oil slick promotes the accumulation of residues in the water reservoir, thereby necessitating more frequent cleaning of the dispenser.

In alternative illustrative embodiments, an ultrasonic nebulizer or any other suitable device for emitting one or more materials as a mist, may be positioned outside of the reservoir 54 and not submerged within the water 56. In such an embodiment, the water 56 (and any aroma chemicals entrained therein) may be fed to the nebulizer. Water mist particles may then be directed at the cartridge 70 or through a tortuous path including that knocks down or filters out the larger water mist particles. A volatile material cartridge may be disposed within the tortuous path such that the water mist particles contact the volatile material and entrain the volatile material therein.

In alternative illustrative embodiments, a frame or other device for holding a cartridge or refill may be sold or provided to users of humidifiers for attachment to their humidifiers. In illustrative embodiments, the frame may be adapted for attachment to a portion of a humidifier or other water and/or volatile material dispensing device. Cartridges including one or more volatile materials may be attached to the frame for volatilization thereof. The frame may be sold as a kit, for example with one or more adapters for attaching the frame to one or more humidifiers or other device(s). The kit may also include one or more volatile material cartridges. The kit may be universal in that it may allow for attachment of the frame to multiple devices and/or the kit may be individually tailored for a single device.

Any of the embodiments described herein may be modified to include any of the structures or methodologies disclosed in connection with other embodiments.

Further, although directional terminology, such as front, back, top, bottom, upper, lower, etc. may be used throughout the present specification, it should be understood that such terms are not limiting and are only utilized herein to convey the orientation of different elements with respect to one another.

All documents cited in the Detailed Description are, in relevant part, incorporated herein by reference; the citation of any document is not to be construed as an admission that it is prior art with respect to the present disclosure.

INDUSTRIAL APPLICABILITY

The present invention provides volatile material dispensers for mixing of water and volatile materials, for example, fragrances containing one or more aroma chemicals. One of the advantages of such a dispenser, which includes fragrance-infused water, is that no surfactants or solvents are necessary because the fragrance-infused water for emission is created on demand or as needed. The fragrance-infused water only needs to exist as a dispersion in the air and not as a stable, single-phase system that is designed and needs to maintain its integrity through a long and unpredictable distribution channel.

Numerous modifications to the present disclosure will be apparent to those skilled in the art in view of the foregoing description. Accordingly, this description is to be construed as illustrative only and is presented for the purpose of enabling those skilled in the art to make and use the embodiments of the disclosure and to teach the best mode of carrying out same. The exclusive rights to all modifications which come within the scope of the appended claims are reserved.

We claim:

1. A method of dispensing a fragrance having at least one aroma chemical, the method comprising the steps of:
   providing a frame adapted to be attached to a dispenser for dispensing fluids and a cartridge including a volatile material containing a fragrance comprising at least one aroma chemical, wherein the cartridge is adapted for attachment to the frame;
   nebulizing water to create nebulized water particles;
   directing the nebulized water particles at the cartridge; and
   entraining volatile material from the cartridge in at least some of the nebulized water particles upon collision with the cartridge to create volatile material-infused water particles.

2. The method of dispensing of claim 1, wherein the frame is attached to a dispenser and, after the nebulized water particles collide with the cartridge, some of the volatile material-infused water particles travel out of the dispenser and other of the volatile material-infused water particles condense on the cartridge and drip into a reservoir of the dispenser.

3. The method of dispensing of claim 1, further including the steps of:
   providing a dispenser including a housing having a reservoir adapted to hold water and a nebulizer in communication with the reservoir and the water within the reservoir;
   positioning the nebulizer within a bottom wall of the reservoir;
   spacing the cartridge from the bottom wall of the reservoir along a longitudinal axis of the dispenser; and
   positioning the cartridge at an angle of between about −15 degrees and about 15 degrees with respect to a horizontal plane that is orthogonal to the longitudinal axis and parallel to the bottom wall of the reservoir.

4. The method of dispensing of claim 3, wherein the step of positioning the cartridge includes positioning the cartridge at an angle of between about −5 degrees and about 5 degrees with respect to the horizontal plane that is orthogonal to the longitudinal axis and parallel to the bottom wall of the reservoir.

5. The method of dispensing of claim 2, further including the steps of:
   providing a fragrance with a plurality of aroma chemicals in the volatile material within the cartridge; and
   passively emitting the aroma chemicals having a high volatility and a low solubility.

6. The method of dispensing of claim 5, further including the step of:
   nebulizing volatile material-infused water particles having aroma chemicals with a low volatility and a high solubility after the volatile-material infused water particles have returned to the reservoir.

7. The method of dispensing of claim 6, wherein aroma chemicals having a low volatility and a low solubility and aroma chemicals having a high volatility and a high solubility are emitted in a manner that creates a least amount of resistance.

8. A volatile material dispenser, the dispenser including:
   a frame adapted to be attached to a dispenser having an ultrasonic nebulizer for dispensing fluids; and
   a cartridge containing a volatile material and adapted to be attached to the frame, wherein the frame is adapted to position the cartridge within the dispenser such that cartridge is in a path of nebulized fluid particles, whereby the cartridge acts as a baffle that filters out larger nebulized fluid particles emitted by the ultrasonic nebulizer.

9. The volatile material dispenser of claim 8, further including:
   a dispenser including a housing having a reservoir adapted to hold water;
   an ultrasonic nebulizer in communication with the reservoir and the water within the reservoir, wherein the ultrasonic nebulizer is adapted to volatilize and emit the water as nebulized water particles;

wherein the frame is attached to a portion of the dispenser, the cartridge is attached to the frame, the ultrasonic nebulizer is disposed in a bottom wall of the reservoir, and the water is positioned in the reservoir between the ultrasonic nebulizer and the cartridge.

10. The volatile material dispenser of claim 9, wherein the bottom wall of the reservoir and the cartridge are spaced from one another along a longitudinal axis of the dispenser, the bottom wall of the reservoir is generally orthogonal to the longitudinal axis, and the cartridge is disposed at an angle of between about −15 degrees and about 15 degrees with respect to a horizontal plane that is orthogonal to the longitudinal axis and parallel to the bottom wall of the reservoir.

11. The volatile material dispenser of claim 10, wherein the cartridge is disposed at an angle of between about −5 degrees and about 5 degrees with respect to the horizontal plane that is orthogonal to the longitudinal axis and parallel to the bottom wall of the reservoir.

12. The volatile material dispenser of claim 9, wherein the cartridge includes a container holding the volatile material and a non-porous permeable membrane covering the container and holding the volatile material within the container.

13. The volatile material dispensing of claim 12, wherein the cartridge is positioned in the volatile material dispenser with the non-permeable membrane facing the water within the reservoir and further facing the ultrasonic nebulizer.

14. The volatile material dispenser of claim 13, wherein the frame includes at least one orienting feature that ensures the cartridge is inserted into the frame with the non-porous permeable membrane facing the water within the reservoir and facing the ultrasonic nebulizer.

15. The volatile material dispenser of claim 9, further including a blower for moving volatile material directly from the cartridge and for moving volatile material-infused water particles out of the dispenser.

16. The volatile material dispenser of claim 8, wherein the volatile material in the cartridge contains a fragrance comprising at least one aroma chemical.

17. The volatile material dispenser of claim 16, wherein the volatile material in the cartridge is free of solvents and surfactants.

18. A volatile material dispenser, the dispenser including:
a housing having a reservoir adapted to hold water;
an ultrasonic nebulizer in communication with the reservoir and the water within the reservoir, wherein the ultrasonic nebulizer is adapted to volatilize and emit the water as nebulized water particles;
a cartridge containing a volatile material and positioned such that nebulized water particles from the ultrasonic nebulizer impinge upon the cartridge and entrain volatile material within the nebulized water particles, wherein the volatile material comprises a fragrance with at least one aroma chemical and the volatile material is free of solvents and surfactants.

19. The volatile material dispenser of claim 18, wherein the ultrasonic nebulizer is disposed in a bottom wall of the reservoir, the bottom wall of the reservoir and the cartridge are spaced from one another along a longitudinal axis of the dispenser, the bottom wall of the reservoir is generally orthogonal to the longitudinal axis, and the cartridge is disposed at an angle of between about −15 degrees and about 15 degrees with respect to a horizontal plane that is orthogonal to the longitudinal axis and parallel to the bottom wall of the reservoir.

20. The volatile material dispenser of claim 18, wherein the cartridge includes a container holding the volatile material and a non-porous permeable membrane covering the container and holding the volatile material within the container and the cartridge is positioned in the volatile material dispenser with the non-porous permeable membrane facing the water and the ultrasonic nebulizer.

* * * * *